United States Patent
Lechot

(10) Patent No.: US 7,955,323 B2
(45) Date of Patent: *Jun. 7, 2011

(54) INSTRUMENT HOLDER AND METHOD FOR A SURGICAL INSTRUMENT HAVING A PARK POSITION

(75) Inventor: André Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 1013 days.

This patent is subject to a terminal disclaimer.

(21) Appl. No.: 11/688,199

(22) Filed: Mar. 19, 2007

(65) Prior Publication Data

US 2007/0203477 A1 Aug. 30, 2007

Related U.S. Application Data

(63) Continuation of application No. PCT/IB2004/003676, filed on Nov. 10, 2004, and a continuation-in-part of application No. 10/429,897, filed on May 5, 2003, now Pat. No. 7,296,804, and a continuation-in-part of application No. 10/391,464, filed on Mar. 18, 2003, now Pat. No. 7,056,317, which is a continuation-in-part of application No. 09/902,369, filed on Jul. 9, 2001, now Pat. No. 6,540,739, which is a continuation of application No. 09/602,341, filed on Jun. 24, 2000, now Pat. No. 6,264,647.

(60) Provisional application No. 60/783,980, filed on Mar. 20, 2006.

(51) Int. Cl.
*A61B 17/00* (2006.01)

(52) U.S. Cl. .................................. 606/1; 606/79; 606/80
(58) Field of Classification Search ........................ None
See application file for complete search history.

(56) References Cited

U.S. PATENT DOCUMENTS

| 5,062,749 | A | * | 11/1991 | Sheets | 279/75 |
| 5,499,985 | A | * | 3/1996 | Hein et al. | 606/99 |
| 5,658,290 | A | | 8/1997 | Lechot | |
| 2005/0124981 | A1 | | 6/2005 | Desarzens et al. | |

FOREIGN PATENT DOCUMENTS

| WO | WO 2004/100805 | 11/2004 |
| WO | WO 2005/044114 | 5/2005 |

* cited by examiner

*Primary Examiner* — Henry M Johnson, III
*Assistant Examiner* — Lynsey Crandall
(74) *Attorney, Agent, or Firm* — Michael F. Scalise

(57) ABSTRACT

A surgical instrument holder has a head assembly and a drive spindle assembly. The head has a second coupling end with a coupling device and interface for receiving and holding a surgical instrument. The instrument is held by a releasable locking mechanism having a ring slideably biased against the coupling device by a spring, and a connection device retaining the spring in a fixed position during use. The spindle assembly has a drive spindle rotatably housed in a cylindrical tube. The connection device provides a quick-release connection between the head and drive spindle assemblies, such that unlocking the connection device enables quick disassembly of the connection for cleaning and component sterilization. A method of use of the instrument holder allows the surgical instrument to be installed through an incision in a least invasive orientation separate from the holder.

23 Claims, 7 Drawing Sheets

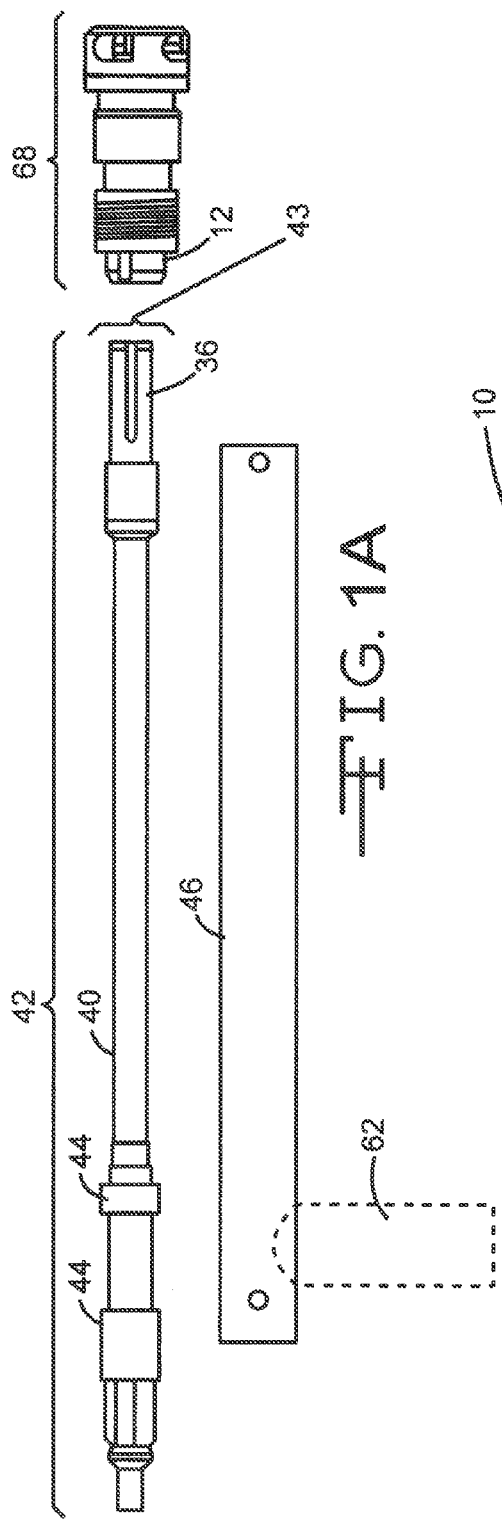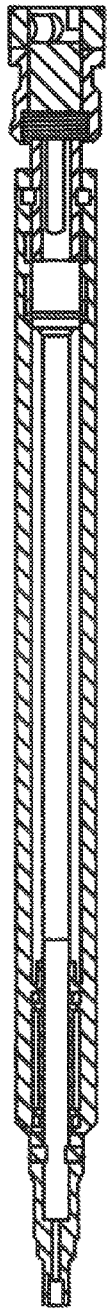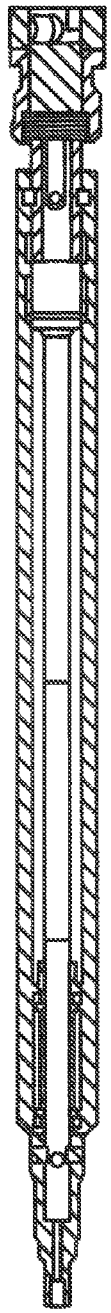

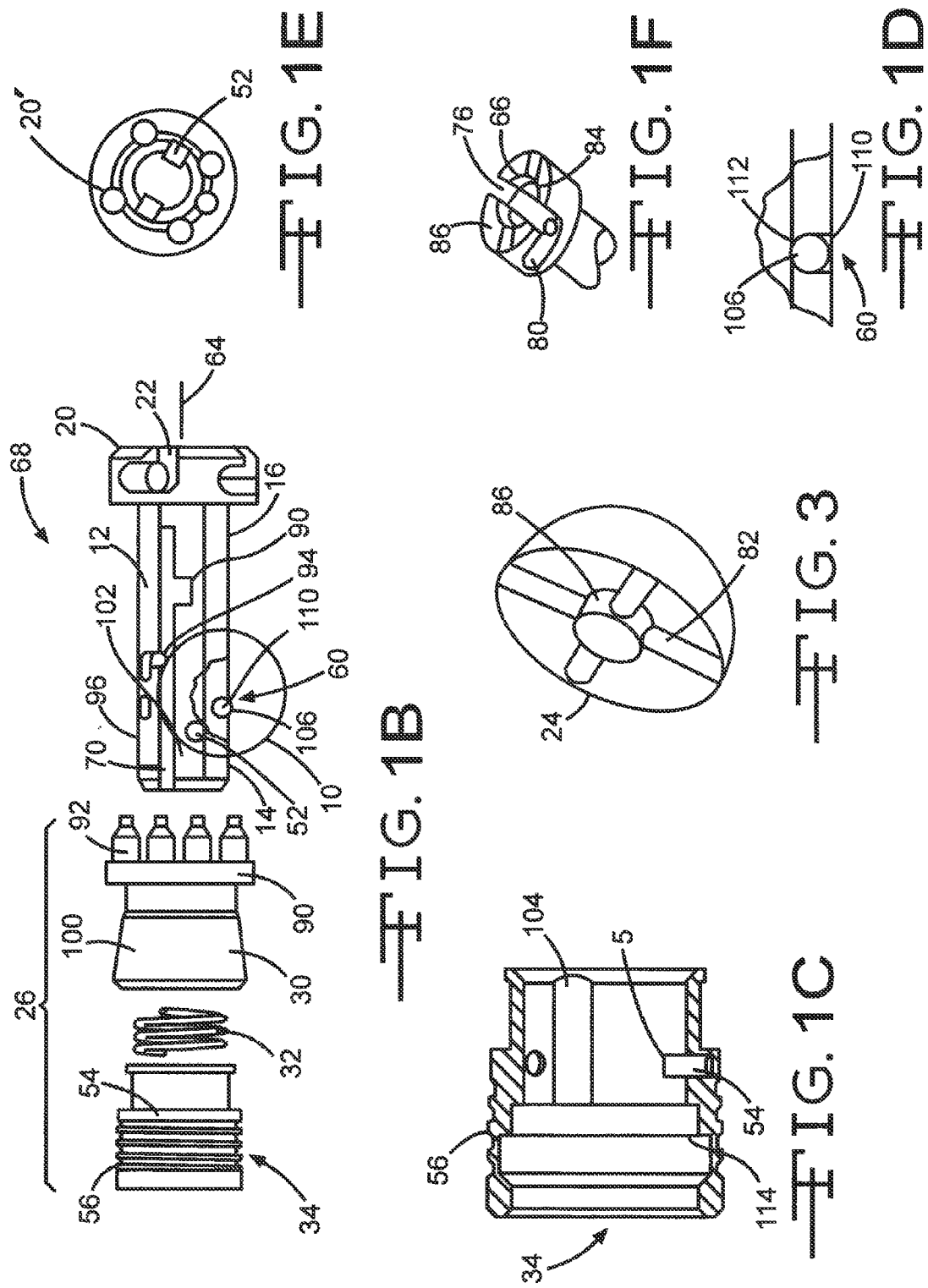

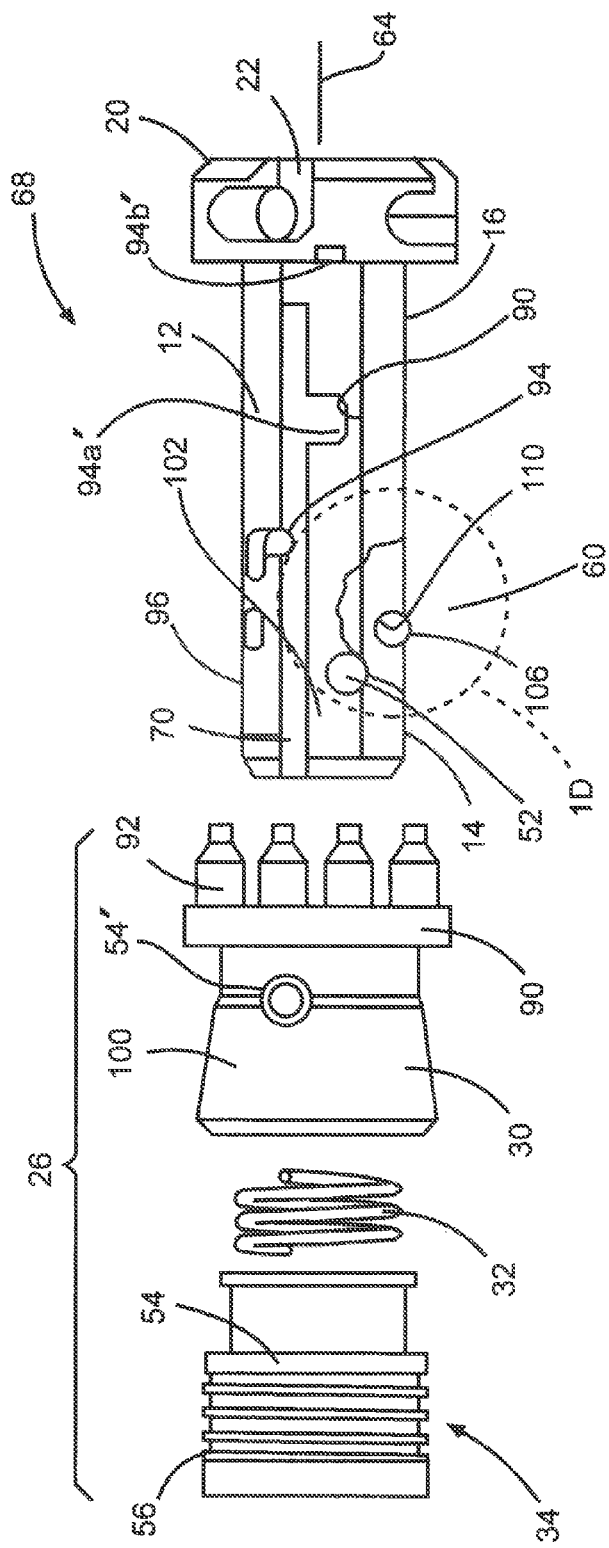

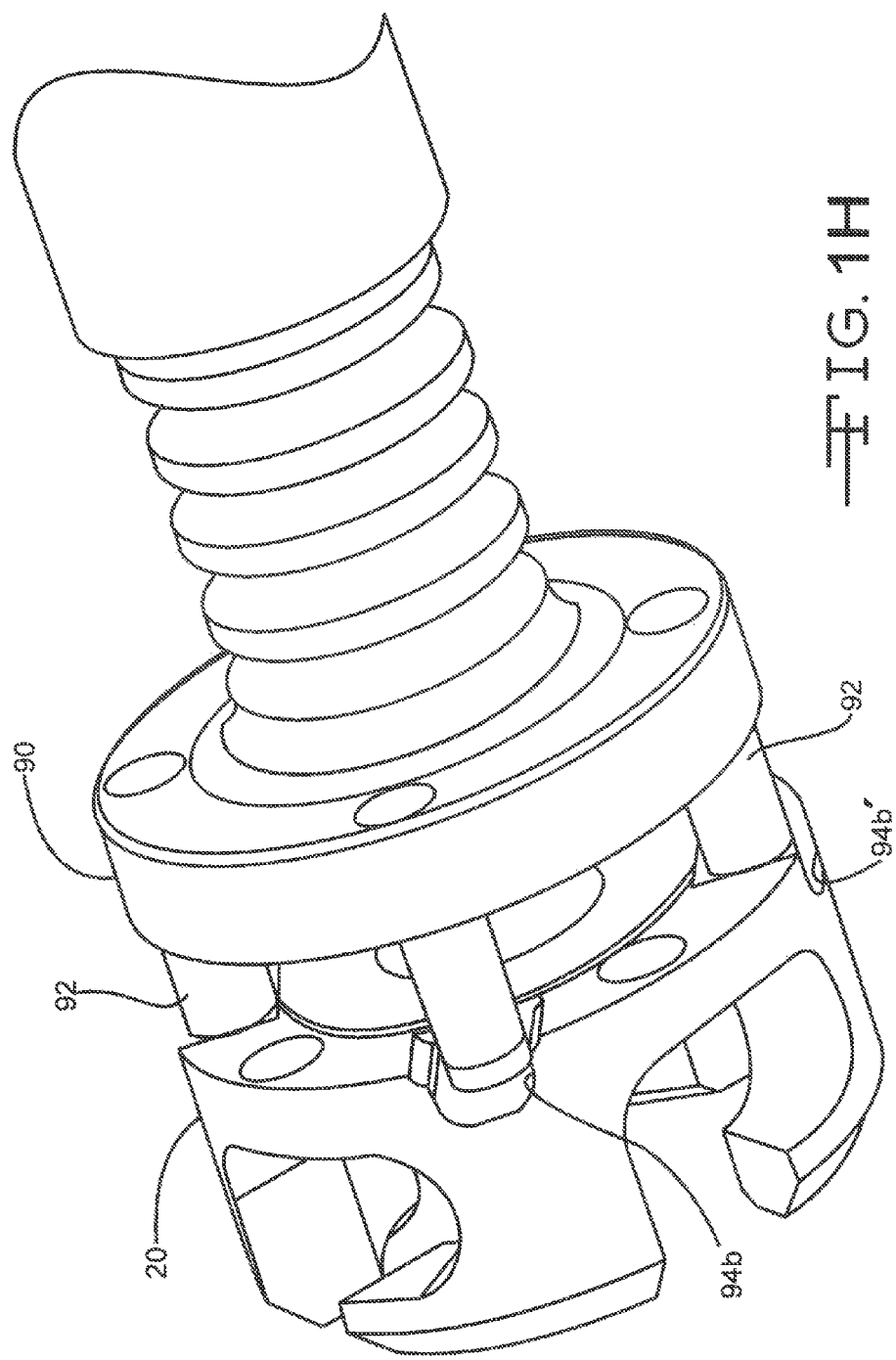

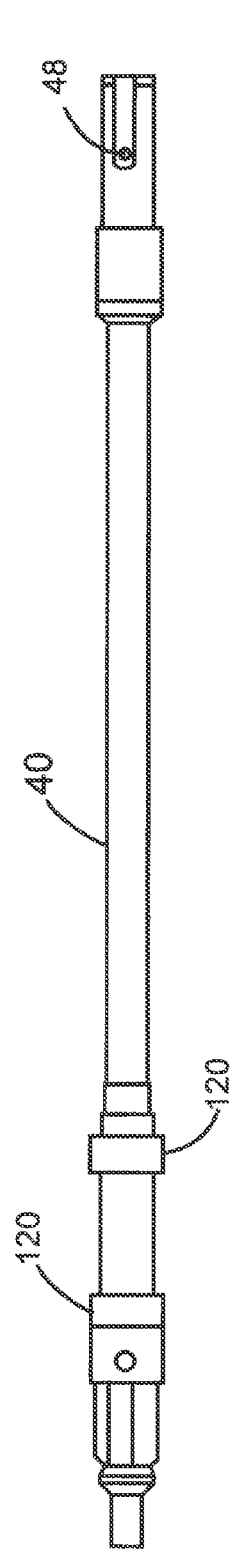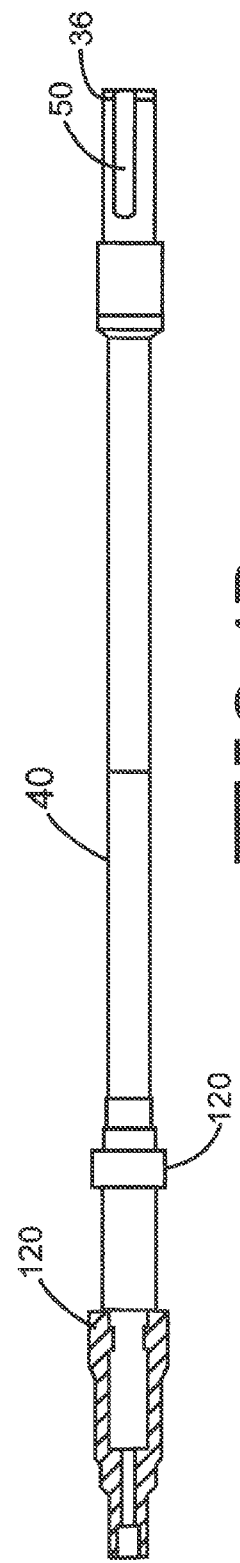
FIG. 4A
FIG. 4B

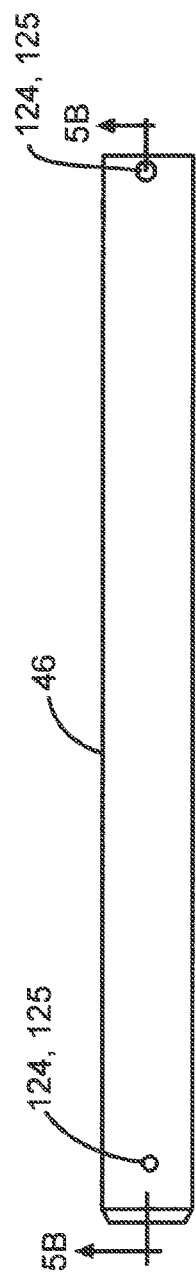
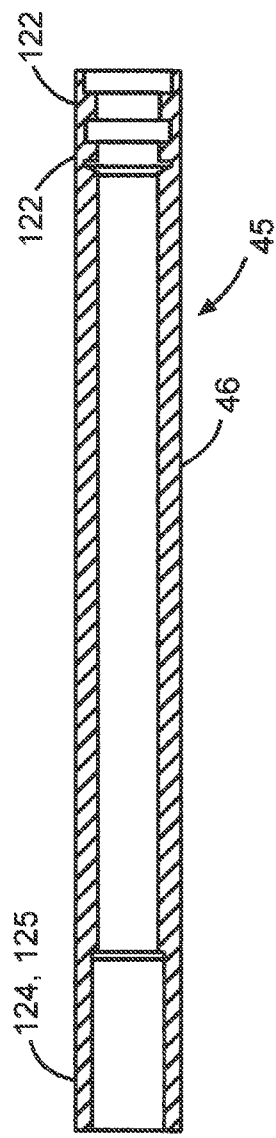
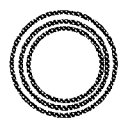
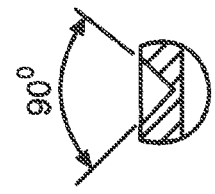
FIG. 5A
FIG. 5B
FIG. 5C
FIG. 5D

INSTRUMENT HOLDER AND METHOD FOR A SURGICAL INSTRUMENT HAVING A PARK POSITION

The present application claims the benefit of prior filed U.S. Provisional Application Ser. No. 60/783,980 filed 20 Mar. 2006; and is a continuation-in-part of application Ser. No. 10/391,464 filed 18 Mar. 2003 (now U.S. Pat. No. 7,056, 317), which is a continuation-in-part of application Ser. No. 09/902,369 filed 9 Jul. 2001 (now U.S. Pat. No. 6,540,739), which in turn is a continuation of application Ser. No. 09/602, 341 filed 24 Jun. 2000 (now U.S. Pat. No. 6,264,647); and application Ser. No. PCT/IB2004/003676 filed 10 Nov. 2004; and application Ser. No. 10/429,897 filed 5 May 2003 now U.S. Pat. No. 7,296,804 to which the present application is a regular US national application, and which claimed applications are fully incorporated herein by reference.

FIELD OF THE INVENTION

The present invention is in the field of orthopedic surgical instrumentation for particular use in a surgical procedure on bone structure, and relates to handles and/or tool holders attachable to surgical cutting tools adapted to cut into bone or associated softer bone like tissues of the body. More specifically, the present invention relates to surgical tool handles having a tool holder mechanism that can be attached to and detached from a surgical tool while the surgical cutting tool is in situ at a surgical site in the patient.

BACKGROUND

A surgical bone cutting instrument, for example for preparing for the fitting of a hip prosthesis, works in a medium which causes considerable fouling of the instrument and the instrument holder. Moreover, a surgical instrument holder must be cleaned very frequently and very carefully in order to avoid any risk of infection. However, cleaning of surgical instruments is difficult, in particular cleaning of the space between the shank and the locking component on account of the presence of bone debris and coagulated blood.

Further, in minimally invasive surgical procedures, the surgeon very often first inserts the surgical cutting tool through an incision in an orientation such that it does the least amount of damage to soft tissue upon passing through to the site of its intended use. Then the surgeon inserts the driving tool and connects it to the cutting tool inside the body cavity as a final assembly operation. For removal, it is preferable to reverse the procedure. However, there are instances where it would be advantageous to be able to quickly and easily remove the driving tool from the work site while the surgical tool remains in situ in the body. Particularly where the patient is obese or where the anatomical object to be treated is deep within the body, the above-mentioned prior art devices require that the surgeon remove the surgical cutting tool from the body through the incision while the drive handle is still attached to it.

Therefore, what is needed is a surgical instrument holder that provides a mode of operation that permits easy removal and reinstallation of the tool driver and surgical tool while deep in a body cavity.

SUMMARY

An object of the present invention is to provide a surgical tool handle having an instrument holder device that can be attached to and detached from a surgical cutting tool while the cutting tool is in situ at a surgical site in the patient. To this end, the instrument holder according to the invention is distinguished by the fact that a bias spring bears on a ring sliding on the shank, and that the shank and the ring have means of connection that is set into use manually by rotation of the ring. Once set, counter rotation of the ring causes release of the ring and allows the locking component, the spring and the ring to slide freely on the shank for easy cleaning and sterilization. Further, the coupling head of the holder includes means for unlocking and for parking a device in an unlock position, thus enabling easy removal and attachment of the coupling head to a surgical tool deep inside a patient's body.

According to a preferred embodiment of the invention, the shank has, under the head, a section with a diameter greater than the diameter of the rest of the shank, on which section the ring is fixed by a bayonet fastening. The play of the components making up the locking means on the shank permits good cleaning without it being necessary to remove these components completely from the shank. This avoids the risk of losing a component or mixing them up, and it obviates the need to fit the components back onto the shank when reassembling the holder. The fastening and release of the ring is accomplished very quickly and easily, which represents a saving in time. This makes it possible to ensure that a complete kit of instruments is not rendered unusable because of a single component being missing. The head and the fastening and locking means of the instrument can be designed in many ways. These means do not form part of the present invention.

BRIEF DESCRIPTION OF THE DRAWINGS

FIG. 1A is an exploded view of the instrument holder of the invention in the disassembled position.

FIG. 1B is an exploded view of the head of the instrument holder is a disassembled position.

FIG. 1C is a cross-sectional view of the locking ring of the invention.

FIG. 1D is a detail view of the area A of FIG. 1B of the invention.

FIG. 1E is a rear, cross sectional view taken through the pins of the shank of the invention.

FIG. 1F is a perspective view of the head of the head assembly of the invention.

FIG. 1G is an exploded view of the head assembly of the invention.

FIG. 1H is a perspective view of the head assembly of the invention with the Locking device in the parked, "unlock" position.

FIG. 2A is an assembled, cross sectional view of the instrument holder in the locked position, taken through the ball-detents.

FIG. 2B is an assembled, cross sectional view of the instrument holder taken 90 degrees from that of FIG. 2A, in the locked position.

FIG. 3 is a perspective view of a surgical instrument for use with the invention.

FIG. 4A is a side view of a central drive shaft having a bearing attached thereto.

FIG. 4B is a partial cross sectional view of the drive shaft of FIG. 4A.

FIG. 5A is a side view of the spindle cover tube of the invention.

FIG. 5B is a cross sectional side view of the spindle tube of the invention.

FIG. 5C is a front view of the spindle cover tube of the invention.

FIG. 5D is a detail view of a location divot of the invention.

DETAILED DESCRIPTION OF THE INVENTION

Figure 6B:
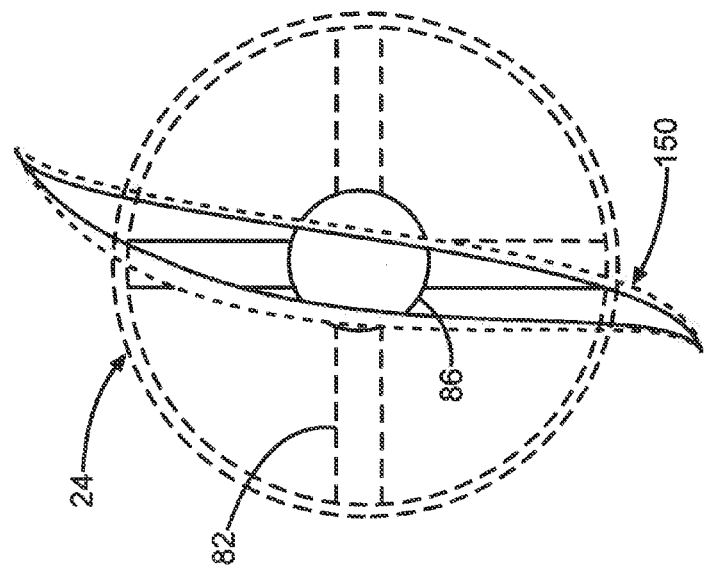
FIG. 6B is a view of the surgical cutting tool of FIG. 6A re-oriented at the surgical work site inside the body of the patient in a presentation allowing attachment of the present instrument holder to the cutting tool.

Referring now to the drawings, the details of preferred embodiments of the present invention are graphically and schematically illustrated. Like elements in the drawings are represented by like numbers.

Referring now to FIGS. 1A-1H, and 2A-2B, a surgical instrument holder 10 is connectable to a spindle assembly 42. The instrument holder 10 has a cylindrical shank 12 at one end of which a coupling head 20 is fixed. See U.S. Pat. No. 5,658,290, for an essentially identical head described therein, the content of which is incorporated by reference thereto. The shank 12 has a driveable end 14 and a coupling end 16. The coupling end 16 is made up of the coupling device 20 having an interface 22 for receiving a surgical instrument 24, shown in FIG. 3. The surgical instrument 24 is held in functional assembly to the coupling device 20 by a releasable locking mechanism 26. The locking mechanism 26 includes a ring 30 slideably disposed about the shank, a spring 32 biased against the coupling device 20 by the ring, and a connection device 34 retaining the ring in a fixed position during use. The spring 32 is preferably a helical compression spring.

The shank 12 is releasably mounted to an end 36 of an elongated drive spindle 40 of a drive spindle assembly 42. The drive spindle assembly 42 has the drive spindle 40, high-precision bearings 44, 120, 122 and a cylindrical tube 46. The drive spindle 40 is supported for rotation within the cylindrical tube 46 by the high-precision bearings 44, 120, 122 disposed there between. The bearings 122 are retained by the shank 12. The bearings 44, 120, 122 precisely control the position of a surgical instrument 24 relative to position sensors 124 mounted on the tube. The end 36 of the drive spindle 40 has a keyway 50 which cooperates with a key or pin 52 on the shank 12 in order to impart a torque into the shank 12 when driving an instrument 24. The shank 12 is locked on the drive spindle 40 via the balls 106, which lock into divots 48 upon actuation by the common connection device 34, thereby providing a common quick-release connection with the shank 12. Thus, unlocking of the connection device 34 enables quick disassembly of the connection device, spring 32, ring 30, and drive spindle assembly 42 for cleaning and component sterilization.

The ring 30 of the releasable locking mechanism 26 is moveable in a locking direction to lock the instrument 24 onto the interface 22. The locking direction is toward the coupling end 16 of the shank 12. The connection device 34 includes at least one pin 54 mounted in a coupling sleeve 56. The spring 32 is biased against the coupling sleeve 56 by the ring 30. The sleeve 56 is slideable about the shank 12 so as to operate a ball-detent 60. The ring 34 locks over the shank 12. Optionally, the shank 12 may have a smaller diameter, or smaller local diameter (for example, by longitudinal flats cut onto the cylindrical surface of the shaft) than the coupling end, so that when the ring 30 is unlocked and slid back along the shank, cleaning access to all surfaces of the locking mechanism is facilitated.

Referring again to FIGS. 1B to 1H, the interface is a recess 22 in the head 20 of the coupling end 16 of the shank 12. The recess 22 is cylindrical and coaxial with a central axis 64 of the shank 12. As shown in FIG. 1F, a chamfered surface 66 is disposed within the recess to align the instrument 24 axially. The interface 22 is a recess intersected by a transverse slot 76 in which a wall 80 of the slot engages a corresponding surface 82 of the instrument 24. The recess 22 includes a seat 84 shaped to receive the hub 83 of the instrument 24 within its circumference 86.

This head 20 has a central recess 84, the head forming a crown 88 around this recess. This crown 88 has four bayonet catches 22 diametrically opposite in pairs. A surgical instrument cutting tool 24 analogous to the reamer shown and described in U.S. Pat. No. 5,658,290 is fixed in these catches 22. The surgical cutting tool 24 is locked in the catches 22 by an annular locking component 30 equipped with a plate 90 having four parallel fingers 92 which pass through the head 20 in order to close the bayonet catches 22, in a manner as is described in U.S. Pat. No. 5,658,290.

The locking component 30 slides on the shank 12. A first bayonet arrangement, including a catch 94, is formed at the end 96 of the shank 12 remote from the head 20. There may be two of more of such catches 94, diametrically opposed to facilitate assembly, as is explained below. A second bayonet arrangement 94a', 94b' is adapted to enable the pins 92 of the component 30 to back out of the holes 20' (see FIG. 1E) and then rotate into catches 94b' (see FIG. 1H) in an open, unlocked and "parked" position. In order to control this movement, a bayonet pin 54', press fit into the locking component 30, rides along the slot or keyway 70 and may be manually guided into a transverse slot 94a'. The assembly is held in place by the force of the spring 32, arranged about the shank 12, biasing the pins 92 of the locking component 30 into the catches 94b'. The helical spring 32 engages in a frustoconical widened part 100 of the locking component 30 and bears against this locking component 30, which otherwise slides freely on the shank 12. The assembly of the instrument holder head 20 is completed by a ring 34 which also slides on the shank 12 and is equipped internally with a radial stud 54 that is captured in a keyway 102, thus permitting the ring to move axially along the shank 12, and eventually into the bayonet recess 94.

The locking device 30 is disposed in the coupling end 16 of the shank 12. The locking device 30 activates at least one ball-detent 60. Preferably, the locking device 30 activates one or more circumferentially spaced apart ball-detents 60. The pin 54 of the connection device 34 cooperates with a guide slot 70 and bayonet landing 94 to lock the device on the shaft 12. The ball-detent 60 is received into a recess 110 in the instrument holder, the locking component 34 sliding over the ball detent 60 to bias a ball 106 into a recess 48 in the drive spindle 40 to lock the shank 12 onto the drive spindle in a manner to lock the assembly 42 including the bearings 44 in place.

Starting from the disassembled position shown in FIGS. 1A-1B, and in order to assemble the instrument holder 10, the locking component 30 is brought under the head, engaging its locking fingers 92 through the head. Then, with the ring 34, the spring 32 is pushed against the locking component 30 and this spring is compressed, at the same time turning the ring 34 axially counterclockwise until its stud 54 engages in the bayonet catch 94 in which the ring 34 locks by holding the ring 34 which is pushed rearward by the spring 32. The instrument holder 10 can then be used as is described in U.S. Pat. No. 5,658,290. The frustoconical widened part 100 provides a grip for the thumb and index finger for pulling the locking component 30 back counter to the action of the spring 32 in order to release the instrument 24 fixed on the instrument holder 10. Note that the ring 34 has two opposing channels or recesses 104 which provide clearance for ball-detents 60 during assembly and disassembly of the head assembly 68.

This is because the balls 106 do not retract all the way into corresponding ball recesses 110 in the shank 12 as they are blocked by a spherical end portion 112 at the bottom of the recess 110. They may also be retained against disassembly by staking the edge of the recess 110 after the ball 106 is placed therein. When the ring 34 is turned, however, the opposing recesses 104 are no longer aligned with the balls 106, thereby enabling the shoulder 114 to be biased against the balls 106 by the force of the spring 32, thus pressing the balls further into their recesses 110 such that the ends of the balls protrude into divots or seats 48 (shown in FIG. 4A) in the end of the spindle 40 which is aligned under the balls by a positioning shoulder and the opposing longitudinally oriented keyways 50 into which pins 52 engage on assembly.

Conversely, in order to disassemble the instrument holder 10, it suffices to first push the ring 34 forward counter to the action of the spring 32. This removes the wedging bias on the balls 106 into seats 48 in the end of the spindle 40, the bias otherwise removing play in the assembly. The surgeon then turns the ring axially clockwise to align the balls 106 with the opposed clearance recesses 104, to enable the balls 106 to further retreat from the recess 110, so as to enable the user to disconnect the spindle assembly 42 from the head assembly 68 by drawing it out as the ring 34 is held against the bias of the spring 32. Concurrently, the turning of the ring 34 in the clockwise direction removes the stud 54 from the bayonet catch 94, thus enabling the surgeon to remove the ring 34 from the shank 12, and then the spring 32, followed by the locking component 30 as well.

As is shown in FIG. 1B, the components 34, 32 and 30 can be completely removed from the shank 12. Note that the ring 34 could also be removably fastened to the shank 12 by screwing, that is to say having a screw thread (not shown) in the ring 34 which threads onto to corresponding threads (not shown) on the shank 12. Note as well that the coupling device 20 and the fingers 92 are only one example of many alternative means of connecting to an instrument 24.

The spindle assembly 42 is also easy to disassemble in that, as shown in FIGS. 4A and 4B, bearings 120 are affixed to the outside surface of the spindle 40 and bearings 122 (shown in FIG. 5B) are affixed to the inside surface of the cover tube 46, thus permitting the tube to be slid off the spindle assembly 42 after removal of the head assembly 68. The spindle tube 46 has position sensor locator divots 124 (wherein a position sensor is disposed) to enable accurate and repeatable positioning of the position sensors on the tube. In an alternate embodiment, a handle 62 is attached to the elongated spindle assembly 42 (see FIG. 1A).

An object of the present invention is to provide optimum conditions for rapid cleaning and precise control of the position of the spindle during operation, in order that position sensors 125 mounted on the spindle cover 46 can transmit accurate position information for computer assisted surgery. To this end, the instrument holder 10 according to the invention has a quick release head 68 which holds the instrument 24, the head 68 being releasably connected to the precision spindle assembly 42 supported in rotation by bearings 44, 120, 122 mounted between the shaft 12 and an outer bearing tube 46. This almost instantaneous disassembly of the component parts of the instrument holder 10 allow it to be thoroughly and quickly cleaned. In turn, the precision spindle 42 may be easily disassembled for cleaning simply by removing the subassembly 43 comprising the spindle 40 and attached bearings 44 from the subassembly 45 comprising the bearing tube 46 and internally mounted bearings 122.

The fastening and release of the ring 34 and thus the assembly/disassembly of the coupling head 68 and spindle assembly 42 takes place instantaneously, which represents a time savings. This helps ensure that a complete kit of instruments 24 is not rendered unusable because of a single component is blocked or inoperative. In an advantage of the invention, the fastening and release of the ring takes place instantaneously, which represents a time savings. This makes it possible to ensure that a complete kit of instruments is not rendered unusable because of a single component being inoperative.

In an object of the invention, an instrument holder 10 is provided which facilitates calibration of CAOS systems by the reproducible repositioning with each attachment and after cleaning. In a further object of the invention, an instrument holder 10 is provided that is simple to disassemble for cleaning without special tools, and which precisely controls the position of the held instrument in order to enable position sensors to transmit position information accurate enough to enable remote, computer assisted orthopedic surgical procedures.

Figure 6A:
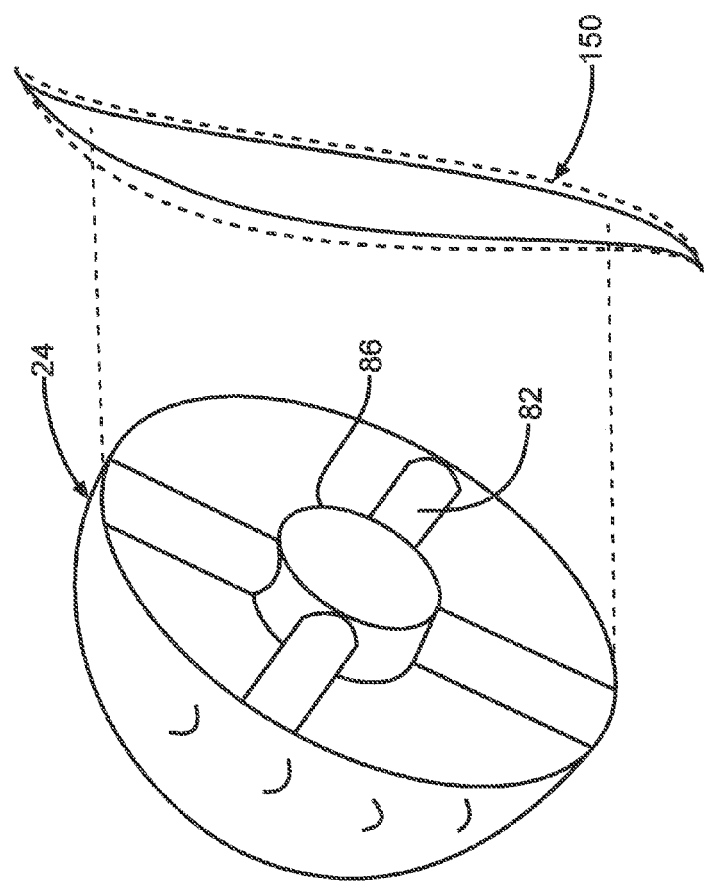
FIG. 6A is view of a surgical cutting tool oriented in a least invasive presentation for insertion through an incision.

A particularly beneficial method for using the present surgical instrument holder 10 is for the in situ engagement of a surgical instrument tool 24 at the work site of a orthopedic bone surgery procedure. This method is particularly useful when is it is desired to keep the incision as small as possible. See FIGS. 6A and 6B. In such a case, presentation of the combination of the instrument tool 24 already attached to a surgical holder has physical aspects that require a larger incision than the physical aspect of presenting only the instrument tool 24 (i.e., separate form the surgical handle). As exemplified in FIG. 6A, the present method of use along with the present tool holder 10 allows presenting only the instrument tool 24, which can be oriented to allow it to be inserted through the incision 120 in a least invasive presentation. After insertion of the instrument tool 24 through the incision 120, the instrument tool 24 is reoriented to its desired presentation to the work site, as exemplified in FIG. 6B.

In practicing the method, a first step is that of inserting the surgical instrument tool 24 through an incision in a least invasive presentation, all the way to the desired surgical work site, and then adjusting orientation/presentation of the surgical instrument tool 24 to a working presentation at the surgical work site. Then using the present surgical instrument holder 10, which is capable of attaching to a surgical instrument tool in situ, advancing the instrument holder 10 through the incision and into contact with the surgical tool 24, and engaging the surgical tool 24 in an operative manner with the instrument holder 10 to accomplish the in situ engagement of the surgical instrument tool 24 with the surgical instrument holder 10. Attaching the surgical tool 24 to the instrument holder 10 is accomplished by engaging the surgical tool 24 in the interface 22 of the coupling end 16 of the instrument holder 10 to provide the in situ engagement of the surgical instrument tool 24 with the surgical instrument holder 10.

Although illustrative embodiments of the invention have been shown and described a wide range of modification, change and substitution is contemplated in the foregoing disclosure and in some instances, some features of the present invention may be employed without a corresponding use of the other features. Accordingly it is appropriate that the appended claims be construed broadly and in a manner consistent with the scope of the invention.

What is claimed is:

1. A surgical instrument holder comprising:
   a) a head assembly having a shank with a first driveable end connectable to a drive spindle assembly so as to transmit torque therethrough, and second coupling end comprising a coupling device having an interface for engaging a surgical instrument tool; and
   b) a releasable coupling locking mechanism disposed about the shank, the locking mechanism having a coupling ring slideably disposed about the shank and normally biased against the coupling device by a spring biased against the coupling ring by a connection device, the connection device releasably held to the shank in a fixed position during use; and
   c) the coupling end including parking and locking features for respectively parking and locking the surgical tool in the interface, the parking feature comprising a catch formed in the coupling end which receives a feature of the coupling ring to permit the releasable coupling locking mechanism to lock in a park position.

2. The surgical instrument holder of claim 1 wherein the ring of the releasable locking mechanism is moveable in a locking direction to lock the instrument onto the interface.

3. The surgical instrument holder of claim 1 wherein the connection device comprises at least one pin mounted in a coupling sleeve against which the spring is biased by the ring, the sleeve being slideable about the shank so as to operate a ball-detent.

4. The surgical instrument holder of claim 1 wherein a handle is attached to the first end of the elongated spindle assembly.

5. The surgical instrument holder of claim 1 wherein spindle assembly further comprises a spindle held within a spindle tube by precision ball bearings which provide precision rotation of the spindle with the tube, and wherein the tube is provided with position sensors, placed at pre-determined locations on the tube, thereby enabling the instrument holder to participate in the communication of position information.

6. The surgical instrument holder of claim 1 wherein the interface is a recess in the coupling end of the shank.

7. The surgical instrument holder of claim 6 wherein the recess is cylindrical and coaxial with a central axis of the shank.

8. The surgical instrument holder of claim 7 wherein a chamfered surface is disposed within the recess to align the surgical instrument axially.

9. The surgical instrument holder of claim 1 wherein the spring is a helical compression spring.

10. The surgical instrument holder of claim 2 wherein the locking device is disposed at the coupling end of the shank.

11. The surgical instrument holder of claim 2 wherein the connection device activates at least one ball-detent.

12. The surgical instrument holder of claim 11 wherein the connection device activates at least two circumferentially spaced apart ball-detents.

13. The surgical instrument holder of claim 2 wherein the locking direction is toward the coupling end of the shank.

14. The surgical instrument holder of claim 1 wherein the connection device cooperates with a bayonet slot to lock the device on the shaft.

15. The surgical instrument holder of claim 14 wherein the pin of the connection device locks in the bayonet slot.

16. The surgical instrument holder of the claim 15 wherein the bayonet slot is disposed on the shank.

17. The surgical instrument holder of claim 11 wherein the ball-detent comprises a ball received into an annular recess in the instrument holder, the locking component sliding over the ball detent to bias a ball into the recess to lock the shank onto the drive spindle in a manner to lock the cover assembly including the bearings in place.

18. The surgical instrument holder of claim 1 wherein the interface is a recess intersected by a transverse slot in which a wall of the slot engages a corresponding surface of the instrument.

19. The surgical instrument holder of claim 18 wherein the recess includes a seat shaped to receive the end of the instrument about its circumference.

20. The surgical instrument holder of claim 1 wherein the shank is hollow along its length so as to provide a channel facilitating chip removal.

21. The surgical instrument holder of claim 1 wherein the tube includes position sensors mounted on the spindle which participate in the communication of position information to a computer to aid in computer assisted surgery.

22. The surgical instrument holder of claim 1 wherein a frustoconical widened part provides a grip for the thumb and index finger for pulling the locking component back counter to the action of the spring in order to release the instrument fixed on the instrument holder.

23. The surgical instrument holder of claim 1 wherein the spindle assembly is disconnectable from the head assembly by means of the common connection device when a user holds the device having an internal stud against a bias of the spring, then turns the ring in such a way that its stud leaves a bayonet catch so as to unlock the ring from the catch, the user being able to remove the ring from the shank, and then the spring, followed by the locking component as well.

* * * * *

UNITED STATES PATENT AND TRADEMARK OFFICE
CERTIFICATE OF CORRECTION

PATENT NO. : 7,955,323 B2  Page 1 of 1
APPLICATION NO. : 11/688199
DATED : June 7, 2011
INVENTOR(S) : Lechot It is certified that error appears in the above-identified patent and that said Letters Patent is hereby corrected as shown below:

Column 1 delete the paragraph spanning lines 5-17:

"The present application claims the benefit of prior filed U.S. Provisional Application Ser. No. 60/783,980 filed 20 Mar. 2006; and is a continuation-in-part of application Ser. No. 10/391,464 filed 18 Mar. 2003 (now U.S. Pat. No. 7,056,317), which is a continuation-in-part of application Ser. No. 09/902,369 filed 9 Jul. 2001 (now U.S. Pat. No. 6,540,739), which in turn is a continuation of application Ser. No. 09/602,341 filed 24 Jun. 2000 (now U.S. Pat. No. 6,264,647); and application Ser. No. PCT/IB2004/003676 filed 10 Nov. 2004; and application Ser. No. 10/429,897 filed 5 May 2003 now U.S. Pat. No. 7,296,804 to which the present application is a regular US national application, and which claimed applications are fully incorporated herein by reference."

Column 1 line 5 insert the following header and paragraph:

--CROSS REFERENCE TO RELATED APPLICATIONS
The present application claims the benefit of prior filed U.S. Provisional Application Ser. No. 60/783,980 filed 20 Mar. 2006; and is a continuation-in-part of application Ser. No. 10/391,464 filed 18 Mar. 2003 (now U.S. Pat. No. 7,056,317), which is a continuation-in-part of application Ser. No. 09/902,369 filed 9 Jul. 2001 (now U.S. Pat. No. 6,540,739), which is a continuation of application Ser. No. 09/602,341 filed 24 Jun. 2000 (now U.S. Pat. No. 6,264,647); and Application No. 11/688,199, filed March 19, 2007 is a continuation-in-part of application Ser. No. 10/429,897 filed 5 May 2003 now U.S. Pat. No. 7,296,804, and the applications claimed above are fully incorporated herein by reference. Application No. PCT/IB2004/003676 is fully incorporated herein by reference.--

Signed and Sealed this
Seventh Day of August, 2012

David J. Kappos
*Director of the United States Patent and Trademark Office*